United States Patent [19]

Zierenberg

[11] 4,261,512

[45] Apr. 14, 1981

[54] INHALATION AEROSOL SPRAY DEVICE

[75] Inventor: Bernd Zierenberg, Ingelheim, Fed. Rep. of Germany

[73] Assignee: Boehringer Ingelheim GmbH, Ingelheim am Rhein, Fed. Rep. of Germany

[21] Appl. No.: 122,839

[22] Filed: Feb. 20, 1980

[30] Foreign Application Priority Data

Feb. 24, 1979 [DE] Fed. Rep. of Germany ....... 2907348

[51] Int. Cl.³ .............................................. B05B 3/14
[52] U.S. Cl. ...................................... 239/102; 427/2; 239/4
[58] Field of Search .................................. 239/102, 4; 261/DIG. 48, DIG. 65

[56] References Cited

U.S. PATENT DOCUMENTS

| | | | |
|---|---|---|---|
| 3,278,165 | 10/1966 | Gaffney | 239/102 |
| 3,812,854 | 5/1974 | Michaels | 239/102 |

FOREIGN PATENT DOCUMENTS 2137083  2/1973  Fed. Rep. of Germany ........... 239/102

*Primary Examiner*—Sam Silverberg
*Attorney, Agent, or Firm*—Hammond & Littell, Weissenberger & Muserlian

[57] ABSTRACT

An improvement in inhalation aerosol spray devices comprising a piezoelectric oscillator connected to an atomizer plate, where the improvement resides in that the working surface of the atomizer plate is coated with a thin elastomer film, whereby the particle spectrum of the aerosol generated by the device is significantly improved.

4 Claims, No Drawings

INHALATION AEROSOL SPRAY DEVICE

This invention relates to an improvement in inhalation aerosol spray devices comprising a piezoelectric oscillator connected to an atomizer plate, where the improvement resides in that the working surface of the atomizer plate is coated with a thin elastomer film, whereby the particle spectrum of the aerosol generated by the device is significantly improved.

BACKGROUND OF THE INVENTION AND THE PRIOR ART

German Offenlegungsschriften Nos. 2,032,433; 2,308,584; 2,445,791; 2,537,765, and 2,637,162, which are incorporated by reference herein, disclose liquid atomizing devices which produce inhalable aerosols from drug-containing solutions. In these known devices the oscillations of a piezoelectric oscillator are transferred to an atomizer plate that divides the drug-containing solution supplied to it into fine droplets which, together with the air, form an aerosol.

When inhalation aerosol sprays are used for the treatment of bronchial spasms, such as asthma, it is important that a sufficient portion of the aerosol droplets are small enough to be transported with the inhaled air into lungs. If the droplets are too large, they settle out in the mouth or in the upper respiratory passages, so that the desired effect is not achieved at all or only to an insufficient degree. The known inhalation spray devices above referred to have the disadvantage that the aerosols which they produce contain too large a portion of relatively big droplets that do not reach the lungs.

OBJECTS OF THE INVENTION

It is an object of the present invention to improve the inhalation aerosol spray devices of the type referred to above so that they will produce aerosols having a more favorable particle spectrum.

Other objects and advantages of the invention will become apparent as the description thereof proceeds.

DESCRIPTION OF THE INVENTION

I have discovered that the above object is achieved by coating the working surface of the atomizer plate of an inhalation aerosol spray device of the piezoelectric oscillator type with a thin elastomer film.

The thickness of the elastomer film is from 50 to 500 $\mu$m, and preferably from 100 to 300 $\mu$m.

The atomizer plate is preferably made of a metal having suitable physical and chemical properties, especially stainless steel. A wide variety of elastomers are suitable for coating the atomizer plate. For instance, the coating may be applied in the form of a concentrated polymer solution from which the solvent is removed by evaporation, or by polymerization of monomers or prepolymers. If the atomizer plate is to be coated with a polyurethane which is formed in situ on the surface, no pre-treatment is necessary except cleaning of the plate surface. If other types of elastomers are used, the elastomer-metal bond can be improved by pre-treatment of the metal surface with a primer.

The following example illustrates the present invention.

EXAMPLE

The working surface of the stainless steel atomizer plate of the inhalation aerosol spray device disclosed in German Offenlegungsschrift No. 2,308,584 was cleaned with methylene chloride, and then, while holding the cleaned plate horizontal, 50 mgm of a moisture-hardenable polyurethane percursor in the form of a 50% solution of diisocyanate phenylmethane (toluene 2,4-diisocyanate) and a polyvalent polyether alcohol in anhydrous toluene adjusted to a viscosity of 23 poises was poured onto it. The solution, which spread evenly over the entire plate surface, was hardened at about 18° C. and 50% relative humidity for 24 hours, resulting in a uniform coating of 200 $\mu$m thickness having a breaking elongation of 340% and a tensile strength of 0.35 kg.

When the thus modified inhalation aerosol spray device was used to treat acetylcholine-induced bronchospasms in dogs with a dose of 200 $\mu$gm of fenoterol per actuation, the same bronchospasmolytic effect was achieved as with the same dose of fenoterol per actuation dispensed from a commercial propellant gas-operated inhalation aerosol spray device. On the other hand, when acetylcholine-induced bronchospasms in dogs were treated with a dose of 200 $\mu$gm of fenoterol per actuation dispensed from an unmodified inhalation aerosol spray device according to German Offenlegungsschrift No. 2,308,584, no bronchospasmolytic effect was achieved.

While the present invention has been illustrated with the aid of a certain specific embodiment thereof, it will be readily apparent to others skilled in the art that the invention is not limited to this particular embodiment, and that various changes and modifications may be made without departing from the spirit of the invention or the scope of the appended claims.

I claim:

1. In an inhalation aerosol spray device comprising a piezoelectric oscillator connected to an atomizer metal plate, the improvement which resides in that the working surface of the atomizer plate is coated with a thin elastomer film having a thickness of 50 to 500 $\mu$m.

2. An inhalation aerosol spray device of claim 1, wherein said elastomer film has a thickness of 100 to 300 $\mu$m.

3. An inhalation aerosol spray device of claim 1, wherein the elastomer is a polyurethane.

4. The method of improving the particle spectrum of an aerosol produced by an inhalation aerosol spray device containing a piezoelectric oscillator connected to an atomizer plate, which comprises coating the working surface of the atomizer metal plate with a thin elastomer film having a thickness of 50 to 500 $\mu$m.

* * * * *